US008066979B1

(12) United States Patent
Dickens et al.

(10) Patent No.: US 8,066,979 B1
(45) Date of Patent: Nov. 29, 2011

(54) **ATTRACTANTS AND REPELLENTS FOR THE TROPICAL ROOT WEEVIL *DIAPREPES ABBREVIATUS***

(75) Inventors: Joseph C. Dickens, Ellicott City, MD (US); Fernando Otalora-Luna, College Park, MD (US); Jennifer A. Hammock, Washington, DC (US); Stephen L. Lapointe, Ormand Beach, FL (US); Rocco T. Alessandro, Fort Pierce, FL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 766 days.

(21) Appl. No.: 12/217,831

(22) Filed: Jul. 9, 2008

Related U.S. Application Data

(60) Provisional application No. 60/949,570, filed on Jul. 13, 2007.

(51) Int. Cl.
*A01N 25/00* (2006.01)
*A01N 31/00* (2006.01)
*A01N 31/08* (2006.01)

(52) U.S. Cl. .......... 424/84; 424/405; 514/731; 514/739; 514/919

(58) Field of Classification Search ............... 424/84
See application file for complete search history.

(56) References Cited

OTHER PUBLICATIONS

Rega et al., "Solid Phase Microextraction (SPME) of Orange Juice Flavor: Odor Representativeness by Direct Gas Chromatography Olfactometry (D-GC-O)", Journal of Agricultural and Food Chemistry, 2003, 51, 7092-7099.*
Jirovetz et al., "Composition, quality control and antimicrobial activity of the essential oil of cumin (*Cuminum cyminum* L.) seeds from Bulgaria that had been stored for up to 36 years", International Journal of Food Science and Technology, 2005, 40, 305-310.*
Werkhoff et al., "Vacuum Headspace Method in Aroma Research: Flavor Chemistry of Yellow Passion Fruits", Journal of Agricultural and Food Chemistry, 1998, 46, 1076-1093.*
Visser, J.H., "Host Odor Perception in Phytophagous Insects", Annual Review of Entomology, vol. 31, 1986, pp. 121-144.
Jones, I.F. et al. "Capture of Diaprepes abbreviatus Coleoptera: Curculionidae in Frass Extract-Baited Traps in Citrus", J. of Economic Entomology, vol. 77, 1984, pp. 334-336.
Raguso, R.A., et al., "A Day in the Life of a Linalool Molecule: Chemical Communication in a Plant-Pollinator System. Part 1: Linalool Biosynthesis in Flowering Plants", Plant Species Biology, vol. 14, 1999, pp. 95-120.
Dickens, J.C., "Orientation of Colorado Potato Beetle to Natural and Synthetic Blends of Volatiles Emitted by Potato Plants", Agricultural and Forest Entomology, vol. 2, (2), 2001, pp. 167-172.
Dickens, J.C., et al., "Green Leaf Volatiles Interrupt Aggregation Pheromone Response in Bark Beetles Infesting Southern Pines", Experientia, vol. 48, 1992, pp. 523-524.
Dickens, J.C., "Green Leaf Volatiles Enhance Aggregation Pheromone of Boll Weevil, *Anthonomus grandis*", Entomol. Exp. Appl., vol. 52, 1989, pp. 191-203.
Reddy, G.V.P., et al., "Development of a Semichemical-Based Trapping Method for the New Guinea Sugarcane Weevil, Rhabdoscelus Obscurus in Guam", JEN, vol. 129, (2), 2005, pp. 65-69.
Altuzar, A., et al., "Electrophysiological and Behavioural Responses of Scyphophorus Acupunctatus (Col., Curulionidae) to Agave Tequilana Volatiles", J. Appl. Entomol., vol. 131, (2), 2007, pp. 121-127.
Jaffe, K., et al., "Chemical Ecology of the Palm Weevil *Rhynchophorus palmarum* (L.) (Coleoptera: Curculionidae): Attraction to Host Plants and to a Male-Produced Aggregation Pheromone", J. of Chemical Ecology, vol. 19, (8), 1993, pp. 1703-1720.
Harari, A.R., et al., "Orientation of Surgarcane Rootstalk Borer Weevil, *Diaprepes abbreviatus*, to Weevil, Frass, and Food Odors", J. of Chemical Ecology, vol. 23, (3), 1997, pp. 857-868.
Otalora-Luna, F., et al., "Appetence Behaviours of the Triatomine Bug Rhodnius Prolixus on a Servosphere in Response to the Host Metabolites Carbon Dioxide and Ammonia", J. Comp. Physiol. A, vol. 190, 2004, pp. 847-854.
Casabianca, H., et al., "Enantiomeric Distribution Studies of Linalool and Linalyl Acetate", J. High Resol. Chromatogr., vol. 21, 1998, pp. 107-112.
Blight, M.M., et al., "An Aggregation Pheromone of Sitona Lineatus", Naturwissenchaften, vol. 71, 1984, p. 480.
Dickens, J.C., et al., "Enhancement of Insect Pheromone Responses by Green Leaf Volatiles", Naturwissenchaften, vol. 77, 1990, pp. 29-31.
Van Tol, R.W.H.M., et al., "Olfactory Responses of the Vine Weevil, Otiorhynchus Sulcatus, to Tree Odours", Physiological Entomology, vol. 27, 2002, pp. 213-222.
Pare, P.W., et al., "De Novo Biosynthesis of Volatiles Induced by Isect Herbivory in Cotton Plants", Plant Physiol., vol. 114., 1997, pp. 1161-1167.
Pare, P.W., et al., "Plant Volatiles as a Defense Against Insect Herbivores", Plant Physiology, vol. 121, 1999, pp. 325-331.

(Continued)

*Primary Examiner* — John Pak
*Assistant Examiner* — Nathan W Schlientz
(74) *Attorney, Agent, or Firm* — John D. Fado; G. Bryon Stover

(57) ABSTRACT

A composition for attracting female tropical root weevils (and/or repelling male tropical root weevils), containing (±)-linalool, cis-3-hexen-1-ol, and carvacrol, and optionally a carrier or carrier material known in the art. A method for attracting female tropical root weevils to an object or area, involving treating the object or area with a composition containing a female tropical root weevil attracting effective amount of (±)-linalool, cis-3-hexen-1-ol, and carvacrol, and optionally a carrier or carrier material. A method for repelling male tropical root weevils from an object or area, involving treating the object or area with a composition containing a male tropical root weevil repelling effective amount of (±)-linalool, cis-3-hexen-1-ol, and carvacrol, and optionally a carrier or carrier material.

11 Claims, 4 Drawing Sheets
(3 of 4 Drawing Sheet(s) Filed in Color)

OTHER PUBLICATIONS

Lewinsohn, E., et al., "Enhanced Levels of the Aroma and Flavor Compound S-Linalool by Metabolic Engineering of the Terpenoid Pathway in Tomato Fruits", Plant Physiology, vol. 127, 2001, pp. 1256-1265.

Raguso, R.A., et al., "A Day in the Life of Linalool Molecule: Chemical Communication in a Plant-Pollinator System. Part1: Linalool Biosynthesis in Flowering Plants" Plant Species Biology, vol. 14, 1999, pp. 95-120.

* cited by examiner

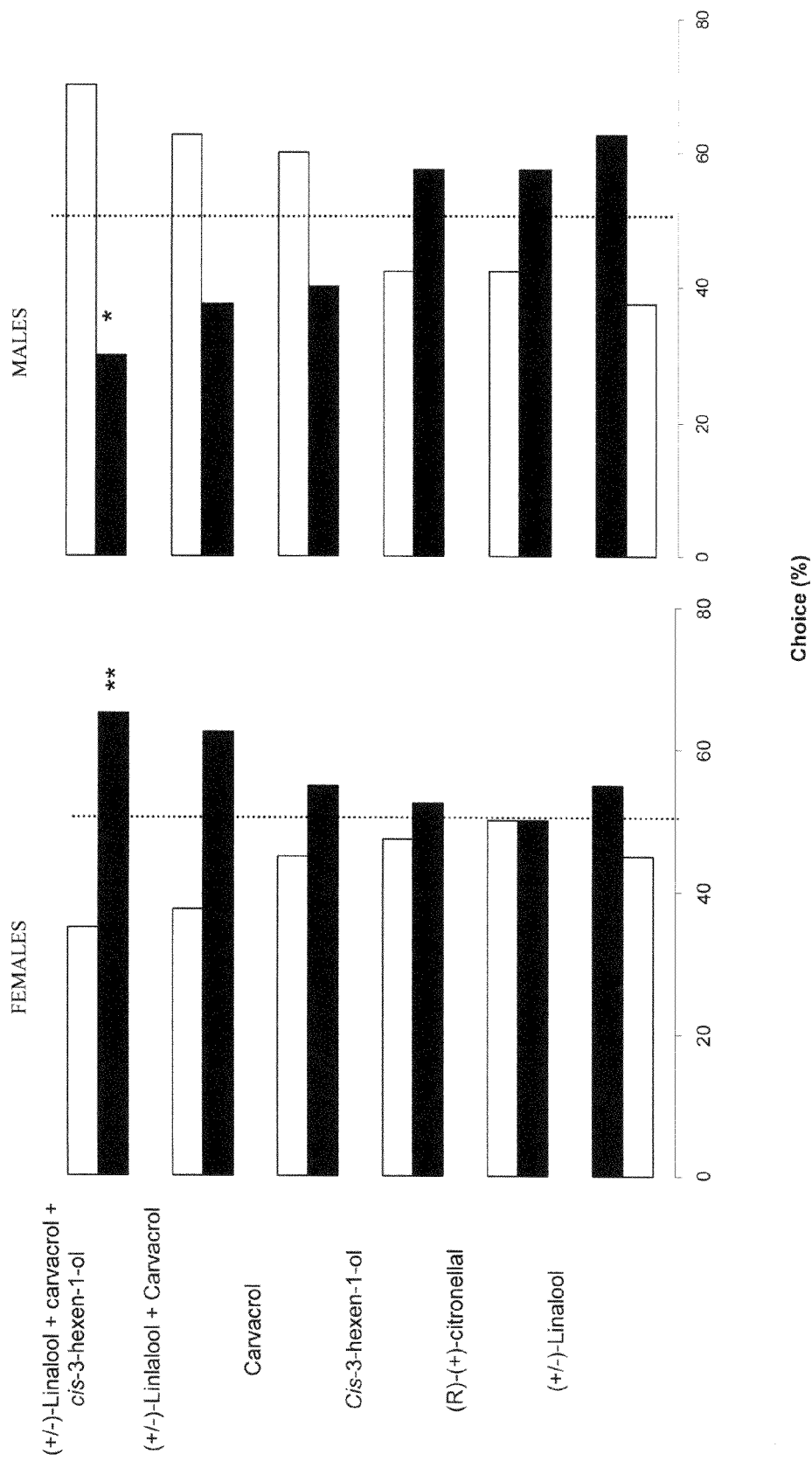

ATTRACTANTS AND REPELLENTS FOR THE TROPICAL ROOT WEEVIL *DIAPREPES ABBREVIATUS*

REFERENCE TO RELATED APPLICATION

This application claims the benefit of U.S. Provisional Application No. 60/949,570, filed 13 Jul. 2007, which is incorporated herein by reference in its entirety.

BACKGROUND OF THE INVENTION

The present invention relates to a composition for attracting female tropical root weevils (and/or repelling male tropical root weevils), containing (±)-linalool, cis-3-hexen-1-ol, and carvacrol, and optionally a carrier or carrier material known in the art.

The present invention also relates to a method for attracting female tropical root weevils to an object or area, involving treating the object or area with a composition containing a female tropical root weevil attracting effective amount of (±)-linalool, cis-3-hexen-1-ol, and carvacrol, and optionally a carrier or carrier material. Furthermore, the present invention relates to a method for repelling male tropical root weevils from an object or area, involving treating the object or area with a composition containing a male tropical root weevil repelling effective amount of (±)-linalool, cis-3-hexen-1-ol, and carvacrol, and optionally a carrier or carrier material.

The tropical root weevil *Diaprepes abbreviatus* (L. 1758) (Coleoptera: Curculionidae) is a phytophagous insect which feeds on at least 270 plant species (Martorell, L. F., Annotated food plant catalog of the insects of Puerto Rico, 1976, Agr. Exp. Stat., University of Puerto Rico; Simpson S. E., et al., Environ. Entomol., 25: 333-349 (1996)). *D. abbreviatus* has been a pest in the Caribbean Islands since the early 19th century, feeding on economically important crops such as guava, coffee, sugar cane, lime, corn, sweet potato, and cotton (Lapointe, S. L., Manejo Integrado de Plagas y Agroecología (Costa Rica), 71: 106-111 (2004)). In 1964, *D. abbreviatus* weevil was introduced into the southern part of United States where it is considered a major threat to orange crops (Lapointe 2004) and ornamental trees (Mannion, C., et al, Florida Entomol., 86(2): 165-173 (2003)). Prior to pupation, *D. abbreviatus* larvae live in the soil and feed on roots causing damage that can result in the death of mature trees. When larval development is completed, adults emerge from the soil to feed upon foliage where aggregation, mate encounter, and oviposition take place. Eventually, new born larvae fall to the ground and enter the soil (Lapointe, S. L., and J. P. Shapiro, Florida Entomol., 82: 291-299 (1999)), thus reinitiating the life cycle.

While some methods are available to control and detect this invasive insect (McCoy, C. W., et al, 2006 Florida Citrus Pest Management Guide: Citrus Root Weevils, IFAS, University of Florida ENY611, pp. 5 (2005)), new knowledge is needed to enhance sustainable pest management strategies.

We have found that a composition containing (±)-linalool, cis-3-hexen-1-ol, and carvacrol, and optionally a carrier or carrier material known in the art, attracts female tropical root weevils and repels male tropical root weevils.

SUMMARY OF THE INVENTION

In accordance with the present invention there is provided a composition for attracting female tropical root weevils (and/or repelling male tropical root weevils), containing (±)-linalool, cis-3-hexen-1-ol, and carvacrol, and optionally a carrier or carrier material known in the art.

Also in accordance with the present invention there is provided a method for attracting female tropical root weevils to an object or area, involving treating the object or area with a female tropical root weevil attracting composition containing a female tropical root weevil attracting effective amount of (±)-linalool, cis-3-hexen-1-ol, and carvacrol, and optionally a carrier or carrier material.

Further in accordance with the present invention there is provided a method for repelling male tropical root weevils from an object or area, involving treating the object or area with a male tropical root weevil repelling composition containing a male tropical root weevil repelling effective amount of (±)-linalool, cis-3-hexen-1-ol, and carvacrol, and optionally a carrier or carrier material.

BRIEF DESCRIPTION OF THE DRAWINGS

The patent or application file contains at least one drawing executed in color. Copies of this patent or patent application publication with color drawing(s) will be provided by the Office upon request and payment of the necessary fees.

FIG. 4 shows responses of *D. abbreviatus* females and males to synthetic analogues of plant volatiles on an open T-track dual choice olfactomer. All compounds were tested at a source load of 25 µg except for carvacrol that was tested at 2.5 µg. Forty insects of each sex were tested for each compound or blend of compounds. Empty bars represent the % of weevils that walked to the clean air; full bars the % of weevils that walked to the odor. When the blend of (+/−)-linalool+carvacrol+cis-3-hexen-1-ol was tested, females walked more to the odor (** $P<0.05$) and males walked more to the clean air (* $P<0.05$).

DETAILED DESCRIPTION OF THE INVENTION

Figure 1:
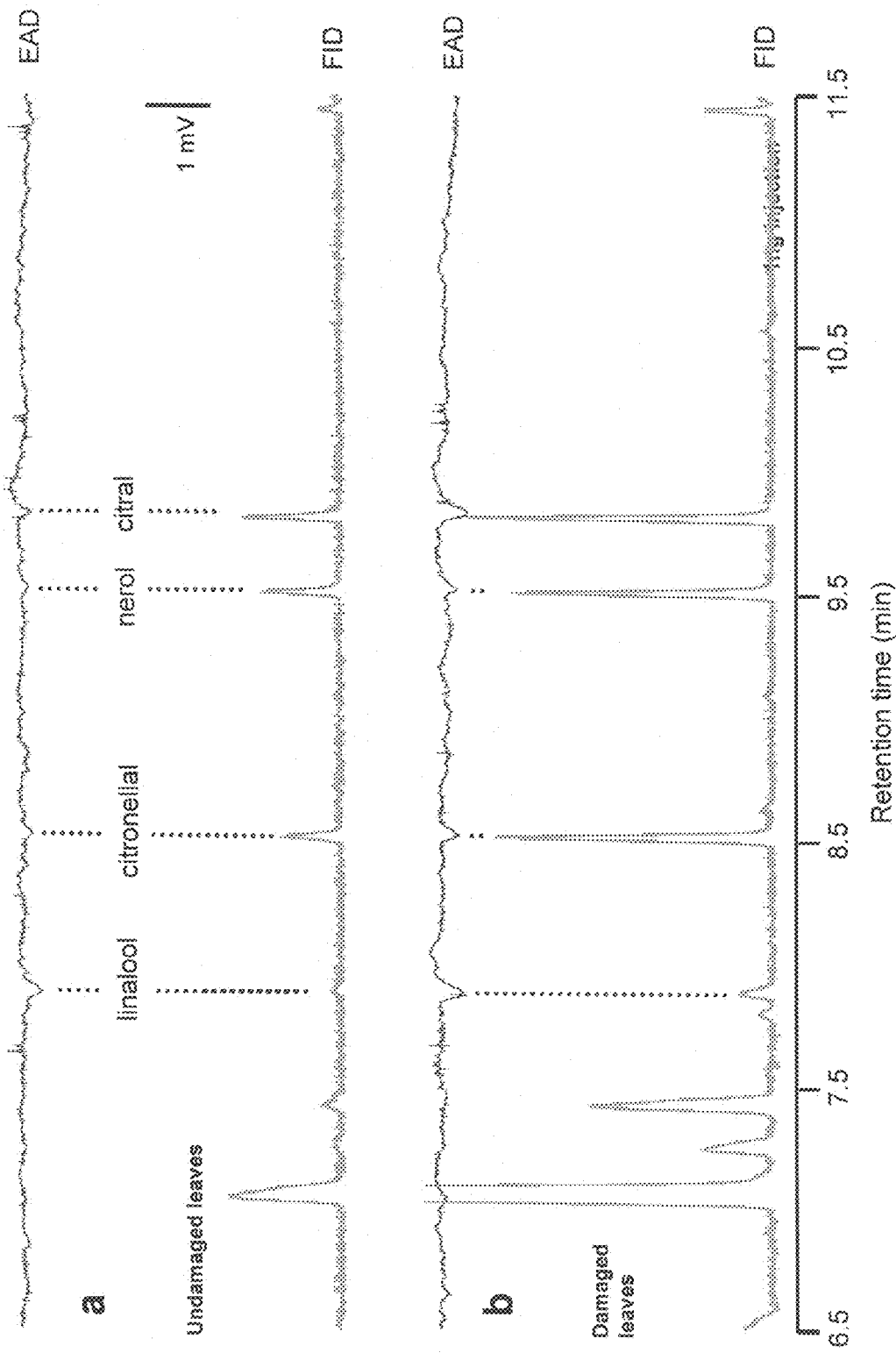
FIG. 1 shows an analysis of citrus volatiles by gas chromatography (GC, HP-5 column) and antennal response (electroantenngraphic detection=EAD, *D. abbreviatus* male antenna). EADs were recorded for citrus odors collected by SPME from the headspace of undamaged (a) and mechanically damaged (b) leaves. EAD-active constituents were confirmed by mass spectrometer.

A composition is disclosed which attracts female tropical root weevils and repels male tropical root weevils, and contains (±)-linalool, cis-3-hexen-1-ol, and carvacrol, and optionally a carrier or carrier material known in the art. The carrier or carrier material may be, for example, agronomically or physiologically or pharmaceutically acceptable carriers or carrier materials.

Also disclosed is a method for attracting female tropical root weevils to an object (e.g., insect trap) or area (e.g., field, orchard), involving treating (or exposing) the object or area with a composition containing a female tropical root weevil attracting effective amount of (±)-linalool, cis-3-hexen-1-ol, and carvacrol, and optionally a carrier or carrier material. The carrier or carrier material may be, for example, agronomically or physiologically or pharmaceutically acceptable carriers or carrier materials.

The attractant of the present invention may be applied with a carrier component. The carrier component can be a liquid or a solid material. As is known in the art, the vehicle or carrier to be used refers to a substrate such as a membrane, hollow fiber, microcapsule, cigarette filter, gel, polymers, or the like. All of these substrates have been used to release insect attractants in general and are well known in the art.

The amount of attractant used will be at least an effective amount. The term "effective amount," as used herein, means the minimum amount of attractant needed to attract the female tropical root weevils to a treated area or object when compared to the same area or object which is untreated. Effective concentrations of the attractant in the compositions may vary between about 0.00001% to about 99.99% (preferably about 0.00001% to about 50%, more preferably about 0.00001% to about 10%, more preferably about 0.00001% to about 1%, more preferably about 0.00001% to about 0.1%, more preferably about 0.00001% to about 0.01%). Of course, the precise amount needed will vary in accordance with the particular attractant composition used; the type of area or object to be treated; the number of days of attractiveness needed; and the environment in which the area or object is located. The precise amount of attractant can easily be determined by one skilled in the art given the teaching of this application. For example, one skilled in the art could follow the procedures utilized below; the attractant would attract more than 50% of the female tropical root weevils and would be statistically significant in comparison to a control. The attractant composition may or may not contain a control agent for tropical root weevils, such as a biological control agent or an insecticide known in the art to kill tropical root weevils. Other compounds may be added to the attractant composition provided they do not substantially interfere with the intended activity of the attractant composition; whether or not a compound interferes with attractant activity can be determined, for example, by the procedure utilized below. Such other compounds could include *D. abbreviatus* aggregation-sex pheromone(s) (Beavers, J. B., et al., Environ. Entomol., 11: 436-439 (1982)). Such other compounds may be present generally from about 0.0025% to about 20% in the composition.

The attractants could be used in pest management strategies: (1) as a component of an attracticide which combines it with a feeding stimulant and lethal doses of insecticide or pathogen. Such an attracticide would not only specifically target tropical root weevil populations but would also result in an overall decrease in application rates for pesticides to crop ecosystems; (2) for monitoring populations of colonizing adult tropical root weevils early in the season; (3) in deployment of the trap crop method of tropical root weevil control; (4) to indicate tropical root weevil movement within fields; or (5) in conjunction with antifeedants (Murray, K. D., et al., Entomol. Exp. Appl., 80: 503-510 (1996)) in "push-pull" strategies of insect management.

Additionally there is disclosed a method for repelling male tropical root weevils from an object or area, involving treating (or exposing) the object or area (e.g., field, orchard) with a composition containing a male tropical root weevil repelling effective amount of (±)-linalool, cis-3-hexen-1-ol, and carvacrol, and optionally a carrier or carrier material. The carrier or carrier material may be, for example, agronomically or physiologically or pharmaceutically acceptable carriers or carrier materials. An insect repellant is any compound or composition which deters insects from a host. Thus the term "repelling" is defined as causing insects (e.g., male tropical root weevils) to make oriented movements away from a source of a chemical repellent (Dethier, V. L., et al., J. Econ. Ent., 53: 134-136 (1960)) and also includes inhibiting feeding by insects when a chemical is present in a place where insects would, in the absence of the chemical, feed.

The repellant of the present invention may be applied with a carrier component. The carrier component can be a liquid or a solid material. As is known in the art, the vehicle or carrier to be used refers to a substrate such as a membrane, hollow fiber, microcapsule, cigarette filter, gel, polymers, or the like. All of these substrates have been used to release insect repellants in general and are well known in the art.

The amount of the repellant used will be at least an effective amount. The term "effective amount," as used herein, means the minimum amount of the compound needed to cause male tropical root weevils to make oriented movements away from a treated area or object when compared to the same area or object which is untreated. Effective concentrations of the repellant in the compositions may vary between about 0.00001% to about 99.99% (preferably about 0.00001% to about 50%, more preferably about 0.00001% to about 10%, more preferably about 0.00001% to about 1%, more preferably about 0.00001% to about 0.1%, more preferably about 0.00001% to about 0.01%). Of course, the precise amount needed will vary in accordance with the particular repellent composition used; the type of area or object to be treated; the number of hours or days of repelling needed; and the environment in which the area or object is located. The precise amount of repellent can easily be determined by one skilled in the art given the teaching of this application. For example, one skilled in the art could follow the procedure utilized below.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Insects: Adults of *Diaprepes abbreviatus* (L. 1758) were obtained from a colony maintained at the U.S. Horticultural Research Laboratory, Orlando, Fla. (Lapointe, S. L., and J. P. Shapiro, Florida Entomol., 82: 291-299 (1999)). Insects were kept in an environmental chamber (12:12 h L:D) at 25° C. and 80% relative humidity, and fed with citrus foliage (*Citrus macrophylla* Wester) until use. Adults used for volatile collections, electrophysiological studies and behavioral experiments were tested at least 20 days after emergence from pupae, when sclerotization of the cuticle, capacity to eat and sexual maturity were completed. Prior to behavioral experiments, insects were starved between 24 and 48 hours. Each individual was used only once.

Volatile collections: Solid-phase microextraction (SPME, Supelco™, USA) was used to collect volatiles for 20 s from 2.4 g of undamaged or mechanically damaged citrus leaves placed into a 250 ml Erlenmeyer flask. Prior to headspace sampling, the fiber was heated in the GC inlet for 10 minutes. The SPME fiber used was polydimethylsiloxane (PDMS) which has an affinity for hydrocarbons and a lower affinity for water, thus being more suitable for sampling in humid environments.

Gas chromatography-linked electroantennogram detection (GC-EAD): The antenna of the insect was employed as a detector in tandem with a high resolution gas chromatography system (GC, Hewlett Packard, 5890A) as in Dickens (Dickens, J. C., Agr. Forest Entomol., 1: 47-54 (1999)) to locate biologically active constituents in volatile collections of plants and candidate chemicals. An adult weevil antenna was mounted between two glass capillaries. Silver wires were inserted into the ends of both glass capillaries. One glass capillary filled with 0.1 M NaCl served as recording electrode holding the tip of the flagellum. The other capillary filled with electrode gel (Spectra 360, Parker Laboratories, USA) served as ground electrode holding the proximal end of the pedicel. The antenna was bathed in a humidified air-stream (60% RH, 23±2° C.) delivered at 30 cm/s (Stimulus Controller CS-05, Syntech) via a stainless steel tube (5 mm internal diameter) whose outlet was approximately 0.5 cm from the preparation. The electrophysiological signal was amplified and conditioned prior to storage and analyses using a computer equipped with GC-EAD 2.3 software (Syntech). Samples were injected into the gas chromatograph with a septum-purged packed column injector and a flame ionization detector (FID) at 245° C. equipped with one of the following J&W Scientific capillary columns: stationary phase DB-WAX-ETR, high polarity, film thickness 0.25 µm, length 30 m, i.d. 0.248 mm or HP-5, low polarity, film thickness 0.25 µm, length 30 m, i.d. 0.251 mm. After an initial temperature of 50° C., which was held for 2 min following injection, the temperature of the GC oven was increased at 15° C./min to 235° C., which was held for 8 min. The enantiomers of linalool present in the odor of citrus were separated for their identification using a β-cyclodextrin column (stationary phase HP-Chiral-20B, mid-polar polarity, film thickness 0.25 µm, length 30 m, i.d. 0.252 mm). Following the injection of the linalool enantiomers, the initial temperature of 50° C. was held for 2 min following injection and then increased at 3° C./min to 180° C. Carrier gas (He) flow was 50 cm/s. The effluent from the column was split using a Gerstel Graph-Pack-3D/2 splitter with a ratio of approximately 1 part to the FID and 4 parts to the electroantennogram detector (EAD). The latter was swept by the humidified air-stream to the electrophysiological preparation from a heated transfer line (Syntech) at 245° C. Volatiles that elicited responses on the antenna were identified by GC-MS (Dickens, J. C., et al., J. Exp. Biol., 4: 309-314 (2002)). The relative proportion of the biologically active compounds detected by FID was calculated using GC-EAD 2.3 software, peaks that did not elicit EAG responses were not considered in such calculations.

Electroantennography (EAG) recordings: For EAGs, an adult weevil antenna was mounted between two electrodes as described above for GC-EAD recordings. EAGs were analyzed using EAG 2.3 software (Syntech).

The following chemicals were serially diluted (ca. 0.01-100 µg) in hexane and tested separately on the antenna: cis-3-hexen-1-ol, trans-2-hexen-1-ol, (±)-linalool, (R)-(−)-linalool, (R)-(+)-citronellal, (S)-(−)-citronellal, cis-geraniol (nerol), trans-geraniol, cis-citral (neral), trans-citral (geranial), and carvacrol. Citral isomers were tested together in a blend. In order to compare activity of (±)-linalool and (R)-(−)-linalool ((S)-(−)-linalool was not available) as well as (R)-(+)-citronellal and (S)-(−)-citronellal, the enantiomers were tested alternatively on the same antenna of female and male weevils. Solvents and synthetic chemicals used in this investigation were ≧97% pure and acquired from Aldrich, Fisher Scientific, Fluka, and Sigma. Nomenclature of chemicals in the text follows that employed by NIST (http://webbook.nist.gov/chemistry/). One microliter of each solution was deposited on a small filter paper strip (0.8×2 cm; Whatman) that was inserted into a Pasteur pipette (cartridge) after solvent evaporation. The tip of the pipette was introduced via a hole in the wall of the stainless steel tube at 3 cm from the preparation. An air current (0.5 s duration, 50 cm/s airspeed; Air Velocity Meter 441S, Kurtz Instruments, USA) swept the chemicals evaporating from the filter paper from the cartridge (Stimulus Controller CS-05, Syntech) to the air-stream in which the antenna was bathed. Interstimulus time intervals of 2-3 min allowed for recovery of the antennal receptors. To allow for changes in sensitivity of an antenna preparation over time, stimulation with a standard compound preceded and followed each stimulus tested. A puff of 1 µg of (R)-(−)-linalool served as standard for EAGs with cis-3-hexen-1-ol and trans-2-hexen-1-ol, and 1 µg of cis-3-hexen-1-ol for EAGs with other compounds. A solvent control consisted of 1 µl of hexane on filter paper. EAGs were standardized by calculating the percent response of the experimental odorant relative to the mean of two responses to the standard preceding and following its presentation. The stimulus threshold was considered to be the concentration at which the lower limit of standard error for a particular mean response did not overlap with the upper limit of the standard error for the response at the lowest concentration tested (Dickens, J. C., Entomol. Exp. Appl., 24: 136-142 (1978)).

Behavioral experiments: An open T-track dual choice olfactometer described by Dickens (1999) was modified as follows. A container (diameter 11 cm, height 8 cm) with petrolatum on its border, to prevent the escape of insects that were placed in its interior, was placed at the bottom of the vertical "T". As *D. abbreviatus* is reluctant to move for long periods (some times hours) after being manipulated, 20-30 insects of the same sex were placed in the container in order to increase chances of observing insects walking. When more than one insect started to climb the "T" tube, the experiment was discarded. Stereotyped behaviors performed by the weevil were recorded using a video camera (Digital Handycam DCR-TVR30).

The following compounds diluted in 25 µl of mineral oil placed on a 4.25 cm filter paper (No. 2, Whatman, England) in a odour-delivery bottle were tested separately in the olfactometer (doses indicated in parenthesis): (±)-linalool (25 µg), (R)-(+)-citronellal (25 µg), carvacrol (25 µg) and cis-3-hexen-1-ol (25 µg). The following blends were also tested: (±)-linalool (25 µg)+carvacrol (2.5 µg) and (±)-linalool (25 µg)+carvacrol (2.5 µg)+cis-3-hexen-1-ol (25 µg). An equal amount of the mineral oil solvent on filter paper was placed in the other side of the olfactometer. In order to observe the behaviour of insects to solvent alone, mineral oil was placed in both odour-delivery bottles. Responses of forty insects (20 females and 20 males) were recorded for each stimulus.

Statistical analysis: EAGs between (±)-linalool and (R)-(−)-linalool as well as between (R)-(+)-citronellal and (S)-(−)-citronellal on the same antenna were compared using the paired Wilcoxon test (Sokal, R. R., and F. J. Rohlf, Biometry, 3rd ed. Freeman, New York (1995)). Relative and absolute proportions of volatiles released by undamaged and damaged citrus leaves were also compared using the paired Wilcoxon test. Insect choices between test and control T-track olfactometer extremes were assessed for significant differences by the hypothesis on binomial proportions based on the standard normal approximation (Brase, C. H., and C. P. Brase, Understanding statistics, 1983, DC Health and Co, Lexington, Mass.). Other behaviors were analyzed using the paired Wilcoxon test and Chi-square test. Statistical analysis was performed using R (version 2.4.0, Vienna, Austria; Ihaka, R., and R. Gentleman, J. Comput. Graph. Stat., 5: 299-314 (1996)).

Results. Electrophysiology. Gas chromatograph-linked electroantennographic detection (GC-EAD). Separation on the GC column revealed the preponderance of monoterpenes in the headspace of citrus leaves (FIG. 1). EAGs were recorded to linalool, citronellal, nerol and trans-citral. There was no difference between the relative proportions emitted by undamaged (FIG. 1a) and mechanically damaged (FIG. 1b) citrus (P=0.875). However, there was a mean 9.74-fold (Standard Error, SE=2.12) increase in the absolute amounts of compounds released by damaged citrus compared to undamaged citrus as detected by FID (P<0.05).

Figure 2:
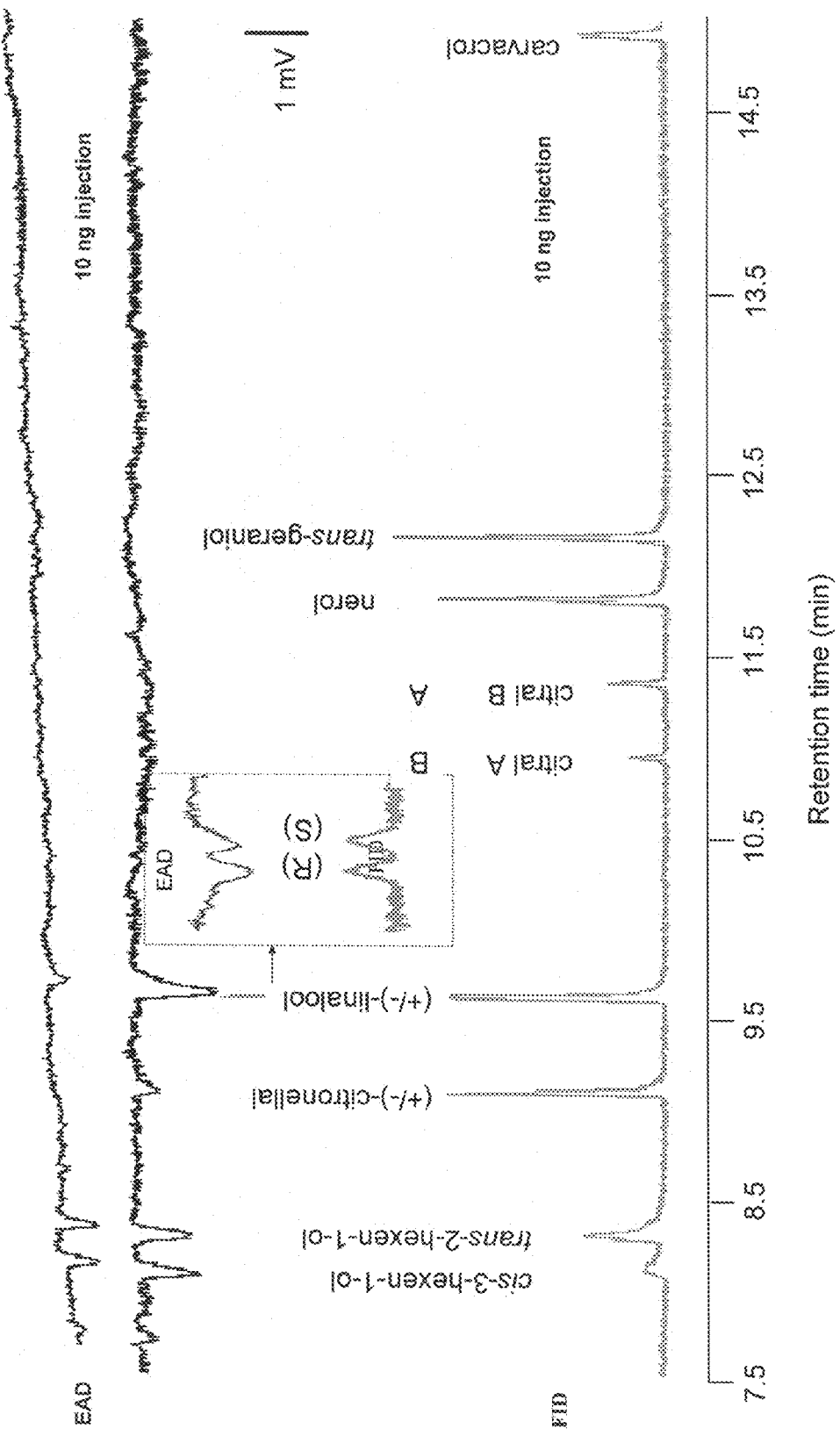
FIG. 2 shows analysis by gas chromatography (GC) linked-electroantennogram detection (EAD) of *D. abbreviatus* male antenna to 1 ng and 10 ng of nine biologically-active compounds injected on a DB-WAXETR column. The two upper traces are the electroantennogram detector responses; the lowest trace is the flame ionization detector response to 10 ng of injected products. Insert shows responses to (R)-(−)- and (S)-(+)-enantiomers of 10 ng of linalool injected in a chiral stationary phase column.

EAGs to (±)-linalool, (±)citronellal, nerol and citral (cis and trans) injected onto the gas chromatograph showed that the responses to citronellal and linalool persisted at 10 ng but antennal responses to citronellal disappeared at 1 ng, the lowest dose injected (FIG. 2). At these injected amounts, no responses were elicited by either nerol and cis-citral or for their geometric isomers geraniol and trans-citral. Cis-3-hexen-1-ol, trans-2-hexen-1-ol, and carvacrol were tested as positive controls and EAGs were recorded only for the two former chemicals.

(R)-(−)-linalool was identified as the enantiomer present in the headspace of citrus leaves using a chiral gas chromatographic column (FIG. 1).

Electroantennograms (EAGs). Mean EAGs of the weevil antenna to the standards cis-3-hexenol-1 and (R)-(−)-linalool diluted 1000-fold in hexane were 1.605±0.200 and 1.750±0.311 mV (mean±SE, n=30), respectively.

EAGs to (±)-linalool and (R)-(−)-linalool did not differ significantly for either males (P=0.095, n=3) or females (P=0.129, n=3). However, EAGs to (R)-(+)-citronellal were larger than for (S)-(−)-citronellal for both males (P<0.05, n=3) and females (P<0.05 n=3).

Figure 3:
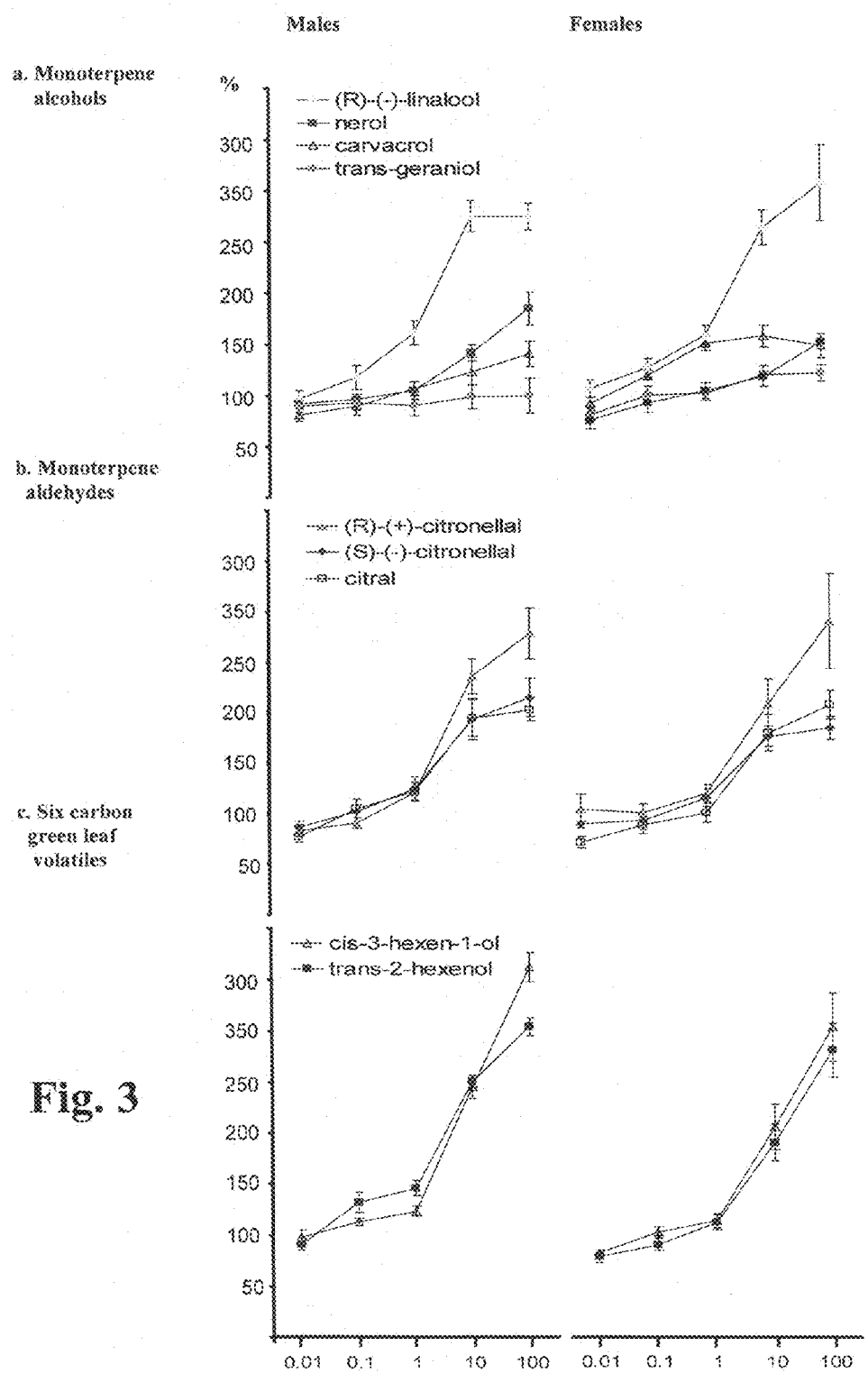
FIG. 3 shows mean electroantennograms of *D. abbreviatus* antennae (n=6 to 10) to chemicals active in gas chromatography linked-electroantennogram detection experiments: (a) monoterpene alcohols, (R)-(−)-linalool, nerol, carvacrol, geraniol; (b) monoterpene aldehydes, (R)-(±)-citronellal, (S)-(−)-citronellal and citral; and (c) six carbon green leaf volatiles, cis-3-hexen-1-ol and trans-2-hexen-1-ol. Responses were normalized using 1 µg of linalool or cis-3-hexen-1-ol on filter paper as reference. Citral refers to a blend of cis- and trans-isomers.

Increments in the amount of most compounds dosed in the stimulus cartridge caused clear increases in the magnitude of EAGs (FIG. 3). This was not the case for trans-geraniol tested on males where no significant increases occurred and on females where EAG increase was not pronounced (FIG. 3, upper traces). EAGs recorded for most compounds showed a marked increase in the response from 1 to 10 μg in the stimulus cartridge but nerol, carvacrol, and trans-geraniol did not share such a pattern (FIG. 3, upper traces). The lowest antenna sensory thresholds, situated around 0.1 μg, were recorded for cis-3-hexen-1-ol, trans-2-hexen-1-ol, citral (cis and trans), and (R)-(−)-linalool tested on females and males as well as for carvacrol and trans-geraniol tested on females and (S)-(−)-citronellal tested on males. EAGs in response to serial dilutions of carvacrol differed with sex: for females, the increase in EAGs was more pronounced than for males from 0.01 μg to 1 μg, and for the two higher stimulus loads (10 μg and 100 μg) this curve reached saturation for females while for males EAGs continued to increase.

Behavior: When both extremes of olfactometer were provided with clean air and solvent, no significant difference was observed between insect choices (P>0.05). Among the individual compounds and blends tested on D. abbreviatus adults, the blend of 25 μg of (±)-linalool, 25 μg of cis-3-hexen-1-ol, and 2.5 μg of carvacrol (weight ratio of 1:1:0.1) resulted in significant attraction for females; the same blend was repellent for males (P>0.05) (FIG. 4).

Discussion. Electrophysiology: Linalool, citronellal, nerol, and trans-citral were identified in citrus leaf volatiles and reliable electrophysiological responses were elicited by them. EAGs for linalool and citronellal were confirmed when their synthetic analogs were tested through GC-EAD, which demonstrated high sensitivity of the antenna for these compounds. Additionally, EAG dose response curves demonstrated the presence of odor receptor cells in the antenna of D. abbreviatus for nerol and citral, both present in the analyzed citrus headspace. However, antennal receptors for the diasteromer of nerol, i.e., trans-geraniol, elicited only small increases in EAGs for females and no increases for males, which suggested that there are surprisingly few receptors on weevils for this volatile.

There was surprisingly consistent antennal response of D. abbreviatus to linalool and D. abbreviatus antennal responses to the linalool enantiomers did not differ. On the other hand, EAGs to citronellal enantiomers were surprisingly larger for (R)-(+)-citronellal than for (S)-(−)-citronellal, which suggested to us that D. abbreviatus possesses some receptors specific for the (R)-(+)-enantiomer. Antennal receptors were also sensitive to cis-3-hexen-1-ol and trans-2-hexen-1-ol. These volatiles showed reliable responses through GC-EAD and dramatic increase in EAGs with increases in stimulus loads, a result that was consistent with an important role for these green leaf volatiles (GLV) for the herbivore D. abbreviatus.

Additionally, antennal sensitivity was surprisingly demonstrated for carvacrol, a plant volatile that was also present in the headspace of D. abbreviatus weevils. Surprising differences in dose-response curves for male and female D. abbreviatus for carvacrol suggested to us a potential role for this aromatic monoterpenoid in sexual behavior. Without being bound by theory, the fact that the dose response curve showed a lower threshold for females, but saturated after 1 μg source dose concentration, may surprisingly indicate a small population of specific receptors for carvacrol on the female antenna.

These results showed for first time that D. abbreviatus adults have olfactory receptors for secondary plant metabolites that belong to diverse chemical groups: (a) alcohol and aldehyde monoterpenes (e.g., linalool, citronellal, nerol, and trans-geraniol), (b) green leaf volatiles (e.g., cis-3-hexen-1-ol and trans-2-hexen-1-ol), and (c) an aromatic monoterpenoid (e.g., carvacrol).

Behavior: As antennal receptors were highly sensitive for linalool, citronellal, cis-3-hexen-1-ol, and carvacrol in electrophysiological experiments, and these compounds represented different chemical groups (FIG. 3), they were tested individually and as components of blends using the T-track olfactometer. Since no apparent difference was surprisingly found between EAGs elicited by linalool enantiomers, a racemic blend ((+/−)-linalool) was used for behavioral experiments. On the other hand, as (R)-(+)-citronellal elicited larger electrophysiological responses than (S)-(−)-citronellal, the former was selected for behavioral experiments. Carvacrol also gained our attention since it surprisingly elicited sexually dimorphic electrophysiological responses. As none of these compounds on their own were attractive at the doses tested, we designed and tested two blends (FIG. 4). Surprisingly only (±)-linalool+cis-3-hexen-1-ol+carvacrol (source doses: 25 μg, 25 μg and 2.5 μg respectively) resulted in significant attraction of females; the same blend was surprisingly repellent to males.

All of the references cited herein, including U.S. Patents, are incorporated by reference in their entirety. Also incorporated by reference in their entirety are the following references: Altuzar, A., et al., J. Appl. Entomol., 131: 121-127 (2007); Blight, M. M., et al., Naturwissenschaften, 71: 480 (1984); Casabianca, H., et al., HRC J. High Res. Chrom., 21: 107-112 (1997); Dickens, J. C., Entomol. Exp. Appl., 52: 191-203 (1984); Dickens, J. C., Agr. Forest Entomol., 1: 47-54 (1999); Dickens, J. C., Agr. Forest Entomol., 2: 167-172 (2000); Dickens, J. C., et al., Experientia, 48: 523-524 (1992); Dickens, J. C., et al., Naturwissenschaften, 77: 29-31 (1990); Harari, A. R., and P. J. Landolt, J. Chem. Eco., 23: 857-868 (1997); Jaffé, K., et al., J. Chem. Eco., 19: 1703-1720 (1993); Jones, I. F., and W. J. Schroeder, J. Econ. Entomol., 77: 334-336 (1984); Lewinshon, E., et al., Plant Physiol., 127: 1256-1265 (2001); Otálora-Luna, F., et al., J. Comp. Physiol. A, 190: 847-54 (2004); Pare, P. W., and J. H. Tumilnson, Plant Physiol., 114: 1161-1167 (1997); Paré, P. W., and J. H. Tumilnson, Plant Physiol., 121: 325-331 (1999); Raguso, R. A., and E. Pichersky, Plant Species Biol., 14: 95-120 (1999); Reddy, G. V. P., et al., J. Appl. Entomol., 129: 65-69 (2005); Tol, R. W. H. M. van, and J. H. Visser, Entomol. Exp. Appl., 102: 49-64 (2002); Visser, J. H., Annu. Rev. Entomol., 31: 124-144 (1986).

Thus, in view of the above, the present invention concerns (in part) the following:

A composition comprising (or consisting essentially of or consisting of) (±)-linalool, cis-3-hexen-1-ol (and/or trans-2-hexen-1-ol), and carvacrol, and optionally a carrier or carrier material.

The above composition according to claim 1, wherein said composition contains from about 0.00001% to about 99.99% by weight (or from about 0.00001% to about 50% or contains from about 0.00001% to about 10% or from about 0.00001% to about 1% or from about 0.00001% to about 0.1% or contains from about 0.00001% to about 0.01%) of said (±)-linalool, cis-3-hexen-1-ol (and/or trans-2-hexen-1-ol), and carvacrol.

The above composition, wherein said composition contains trans-2-hexen-1-ol. The above composition, wherein said composition does not contain trans-2-hexen-1-ol. The above composition, wherein said composition contains (R)-(−)-linalool. The above composition, wherein said composition does not contain (R)-(−)-linalool. The above composition, wherein said composition contains (R)-(+)-citronellal. The above composition, wherein said composition does not contain (R)-(+)-citronellal. The above composition, wherein said composition contains (S)-(−)-citronellal. The above composition, wherein said composition does not contain (S)-(−)-citronellal. The above composition, wherein said composition contains cis-geraniol (nerol). The above composition, wherein said composition does not contain cis-geraniol (nerol). The above composition, wherein said composition contains trans-geraniol. The above composition, wherein said composition does not contain trans-geraniol. The above composition, wherein said composition contains cis-citral (neral). The above composition, wherein said composition does not contain cis-citral (neral). The above composition, wherein said composition contains trans-citral (geranial). The above composition, wherein said composition does not contain trans-citral (geranial).

The above composition, wherein said composition contains an insecticide.

The above composition, wherein said composition contains at least one *Diaprepes abbreviatus* aggregation-sex pheromone.

A method for attracting female tropical root weevils to an object or area, comprising (or consisting essentially of or consisting of) treating said object or area with a female tropical root weevil attracting effective amount of the above composition.

A method for repelling male tropical root weevils from an object or area, comprising (or consisting essentially of or consisting of) treating said object or area with a male tropical root weevil repelling effective amount of the above composition A method for attracting female tropical root weevils to an object or area and/or a method for repelling male tropical root weevils from an object or area, comprising (or consisting essentially of or consisting of) treating said object or area with a female tropical root weevil attracting effective amount of the above composition and/or treating said object or area with a male tropical root weevil repelling effective amount of the above composition.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

|  | hesitation | | rectifying | | reaching | |
|---|---|---|---|---|---|---|
|  | females | males | females | males | females | males |
| (+/−)-Linalool + carvacrol + cis-3-hexen-ol | 77.5 | 82.5 | 42.5 | 47.5 | 47.5 | 45 |
| (+/−)-Linalool + carvacrol | 72.5 | 97.5 | 30 | 62.5 | 70 | 65 |
| Carvacrol | 90 | 95 | 32.5 | 47.5 | 45 | 45 |
| Cis-3-hexen-1-ol | 75 | 85 | 10 | 12.5 | 12.5 | 30 |
| (R)-(+)-citronellal | 95 | 85 | 15 | 5 | 62.5 | 52.5 |
| (+/−)-Linalool | 80 | 82.5 | 22.5 | 25 | 30 | 52.5 |
| Control | 95 | 87.5 | 12.5 | 25 | 20 | 10 |

We claim:

1. A composition comprising (±)-linalool, cis-3-hexen-1-ol, and carvacrol at a weight ratio of 1:1:0.1, and optionally a carrier or carrier material.

2. The composition according to claim 1, wherein said composition contains from about 0.00001% to about 99.99% of said (±)-linalool, cis-3-hexen-1-ol, and carvacrol.

3. The composition according to claim 1, wherein said composition contains from about 0.00001% to about 50% of said (±)-linalool, cis-3-hexen-1-ol, and carvacrol.

4. The composition according to claim 1, wherein said composition contains from about 0.00001% to about 10% of said (±)-linalool, cis-3-hexen-1-ol, and carvacrol.

5. The composition according to claim 1, wherein said composition contains from about 0.00001% to about 1% of said (±)-linalool, cis-3-hexen-1-ol, and carvacrol.

6. The composition according to claim 1, wherein said composition contains from about 0.00001% to about 0.1% of said (±)-linalool, cis-3-hexen-1-ol, and carvacrol.

7. The composition according to claim 1, wherein said composition contains from about 0.00001% to about 0.01% of said (±)-linalool, cis-3-hexen-1-ol, and carvacrol.

8. The composition according to claim 1, wherein said composition contains trans-2-hexen-1-ol.

9. The composition according to claim 1, wherein said composition contains an insecticide.

10. The composition according to claim 1, wherein said composition contains at least one *Diaprepes abbreviatus* aggregation-sex pheromone.

11. A method for attracting female tropical root weevils to an object or area and a method for repelling male tropical root weevils from an object or area, comprising treating said object or area with a female tropical root weevil attracting and male tropical root weevil repelling effective amount of a composition comprising (±)-linalool, cis-3-hexen-1-ol, and carvacrol, and optionally a carrier or carrier material.

* * * * *